United States Patent [19]

Miyake et al.

[11] 4,394,353

[45] Jul. 19, 1983

[54] SEPARATION OF RARE EARTH METALS USING A CATION EXCHANGER

[75] Inventors: Tetsuya Miyake, Tokyo; Kunihiko Takeda, Yokohama; Hatsuki Onitsuka, Fujisawa; Kazuo Okuyama, Yokohama; Yasuki Shimamura, Fuji, all of Japan

[73] Assignee: Asahi Kasei Kogyo Kabushiki Kaisha, Osaka, Japan

[21] Appl. No.: 213,110

[22] Filed: Dec. 4, 1980

[30] Foreign Application Priority Data

| Dec. 19, 1979 | [JP] | Japan | 54-165245 |
| Dec. 20, 1979 | [JP] | Japan | 54-166087 |
| Apr. 30, 1980 | [JP] | Japan | 55-57472 |
| Aug. 5, 1980 | [JP] | Japan | 55-107302 |
| Aug. 8, 1980 | [JP] | Japan | 55-109068 |
| Aug. 9, 1980 | [JP] | Japan | 55-109644 |
| Aug. 11, 1980 | [JP] | Japan | 55-110068 |
| Aug. 12, 1980 | [JP] | Japan | 55-110493 |
| Aug. 27, 1980 | [JP] | Japan | 55-117968 |

[51] Int. Cl.$^3$ .................................................. C01F 17/00
[52] U.S. Cl. .............................. 423/21.5; 423/658.5; 210/674; 210/681
[58] Field of Search .......................... 423/21.5, 658.5; 210/674, 681

[56] References Cited

U.S. PATENT DOCUMENTS

| 2,798,789 | 7/1957 | Spedding et al. | 423/21.5 |
| 2,877,093 | 3/1959 | Tompkins et al. | 423/21.5 |
| 2,897,050 | 7/1959 | Jaffe | 423/21.5 |
| 3,037,841 | 6/1962 | Krumholz et al. | 423/21.5 |
| 3,054,655 | 9/1962 | Krumholz et al. | 423/21.5 |
| 3,167,389 | 1/1965 | Woyski | 423/21.5 |
| 3,228,750 | 1/1966 | Lindstrom et al. | 423/21.5 |

OTHER PUBLICATIONS

Khym, "Analytical Ion-Exchange Procedures in Chemistry and Biology", Prentice-Hall, N.J., 1974, pp. 6-12, 56-67.

Seamster et al., "Chemical Engineering", Aug. 22, 1960, pp. 115-120.

*Primary Examiner*—Herbert T. Carter
*Attorney, Agent, or Firm*—Birch, Stewart, Kolasch & Birch

[57] ABSTRACT

A process for the separation of one rare earth metal from another in a mixture of rare earth metals by chromatographic displacement using a complexing agent and a cation exchanger, which process comprises using a cation exchanger having a micro-void volume void ratio of 0.5 to 0.95, preferably 0.5 to 0.88.

10 Claims, 2 Drawing Figures

SEPARATION OF RARE EARTH METALS USING A CATION EXCHANGER

BACKGROUND OF THE INVENTION

1. Field of the Invention

This invention relates to a process for the separation of rare earth metals by chromatographic displacement using a cation exchanger and a complexing agent.

2. Description of the Prior Art

Rare earth metals can be obtained as a mixture from an ore such as monazite, bastnaesite and xenotime. As a most effective method for the separation of each pure rare earth metal from its mixture, there is a method for the chromatographic separation of rare earth metals by adsorption and development of rare earth metals using a cation exchanger, a retaining agent and a complexing agent.

SUMMARY OF THE INVENTION

According to this invention there is provided an improvement in the separation of rare earth metals by chromatographic displacement using a complexing agent and a cation exchanger which comprises using a cation exchanger having a micro-valid volume ratio of 0.5 to 0.95.

DETAILED DESCRIPTION OF THE INVENTION

Figure 1:
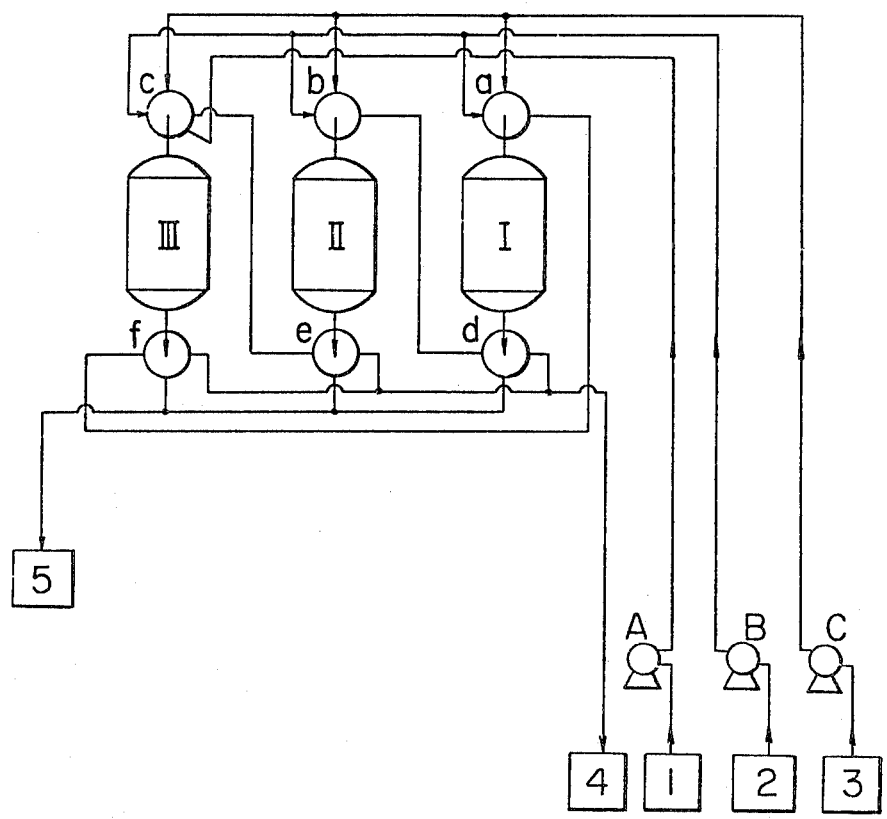
FIG. 1 illustrates the flow diagram of an apparatus of one embodiment of this invention wherein three developing columns are employed.

The term "rare earth metals" as employed in the present specification includes the 15 lanthanide rare earth elements i.e., lanthanum, cerium, praseodymium, neodymium, promethium, samarium, europium, gadolinium, terbium, dysprosium, holmium, erbium, thulium, ytterbium and lutecium; and the elements scandium and yttrium.

The micro-void volume ratio of a cation exchanger is represented by the formula, $Rv = Pv/Sv$ wherein
  Sv is the volume of the cation exchanger, and
  Pv is the pore volume within the cation exchanger particles.

The Pv and Sv are measured as follows;

Measurement of Pv:

(1) An aqueous solution containing 0.1 M/l of hydrogen ion and 0.1 M/l of $PrCl_3$ is supplied to a cation exchanger and the cation exchanger is equilibrated with the aqueous solution.

(2) The equilibrated cation exchanger as obtained in (1) is dehydrated by centrifugal force until the integrated amount of dehydration in the first stage becomes constant as the centrifugal force, i.e., until the rotational number of a dehydrating machine is increased. Generally this centrifugal force corresponds to about 500 to 9,000 r.p.m.

(3) The water of the cation exchanger after the dehydration in (2) is evaporated in a vacuum drier.

(4) The amount of water evaporated in (3) is that of water within pores and designates the pore volume Pv within the cation exchanger particles.

Measurement of Sv:

The true volume of the dried cation exchanger is measured in an apparatus which is free from moisture. Sv designates a total volume of this true volume and the pore volume Pv within the cation exchanger particles.

In this invention it is essential that the micro-void volume ratio of a cation exchanger is 0.5 to 0.95. When the micro-void volume ratio is less than 0.5, the increase in the diffusion coefficient of rare earth metal ions within the cation exchanger is small and a sufficient separation efficiency cannot be accomplished. On the other hand, when the micro-void volume ratio is higher than 0.95, the increase in the diffusion coefficient of rare earth metal ions within the cation exchanger becomes blunt and at the same time, the adsorption amount of the rare earth metal ions is rapidly reduced. As a result, the separation efficiency begins to decrease. A preferred micro-void volume ratio is 0.5 to 0.88 and a more preferred micro-void volume ratio is 0.55 to 0.82.

In order to maintain a high ion exchange rate with an increased degree of cross-linking, it is preferred that the cation exchanger having the above described micro-void volume ratio has a degree of cross-linking of 17 to 80 since the change in volume of the cation exchanger in the development of rare earth metals and in the regeneration of the cation exchanger is small, the pressure drop in the development of rare earth metals is also small and at the same time the separation efficiency is maintained high. When the degree of cross-linking is greater than 80, the amount of adsorption of rare earth metals is too small for practical purposes. A preferred degree of cross-linking is 25 to 40.

The term "degree of cross-linking" as used herein is represented by the following equation:

$$\text{Degree of cross-linking} = \frac{\text{Weight of cross-linkable monomer}}{\text{Total weight of cross-linkable monomer and other monomers for preparing cross-linked polymer}} \times 100$$

Also it is preferred that an average particle diameter of the cation exchanger is 30 $\mu$ to 180 $\mu$ since the ion exchange rate is high and a uniform and stable packed layer of the cation exchanger is obtained.

Furthermore, it is preferred that the cation exchanger of this invention has a particle size distribution where the particle diameter of at least 80% of the entire particles is 0.7 to 1.4 times the average particle diameter. When the cation exchanger having a broad particle size distribution is employed, an nonuniform packed layer of the cation exchanger is easily formed and the overlapping breadth of boundaries of different elements in the rare earth metal adsorption zone tends to become wide.

Also in the separation of rare earth metals and the regeneration of the cation exchanger, small particles of the cation exchanger easily tend to move among large particles and it becomes difficult to obtain a stable packed layer of the cation exchanger. This then results in a decrease in the separation efficiency. It is more preferred that the cation exchanger of this invention has a particle size distribution where the particle diameter of 90% of the entire particles is 0.8 to 1.25 times the average particle diameter.

The particle shape is preferably spherical and at least 90% of the entire particles preferably have a degree of sphericity of at most 2.

The term "degree of simplicity" as used herein represents a ratio of a maximum diameter of one particle passing through the center of gravity of the particle to a minimum diameter of the particle passing through the center of gravity of the particle. For example, when a maximum diameter of one particle through the center of gravity of the particle is 200 μ and a minimum diameter of the particle passing through the center of gravity of the particle is 100 μ, the degree of sphericity is 2.

The cation exchangers which can be employed in this invention may be classified as follows;

Group (i): Ion exchangers in which an ion exchangeable substance is supported on an inorganic supporter. Exemplary supporters include carbon, silica gel, zeolite, activated clay and glass beads, and by adsorption, reaction or graft polymerization, cation exchangeable substances are supported on such inorganic supporters. These ion exchangers are widely used in a specific field of analytical chemistry. The ion exchangers whose supporters are beads and other known supporters as described in Japanese Patent Application (OPI) 32085/1975 and silica gel and other known supporters as described in Japanese Patent Application (OPI) 26386/1977 are advantageously employed in this invention.

Group (ii): Ion exchangers in which an ion exchangeable substance is supported on an organic supporter. Exemplary supporters include high molecular weight polymers such as polyethylene, polypropylene, polystyrene and styrene-divinylbenzene copolymer, and by adsorption, reaction or graft polymerization, cation exchangeable substances are supported on such organic supporters or cation exchangeable substances are reacted onto the surface of such organic supporters. A preferred example of these ion exchangers is a cation exchanger obtained by sulfonating a styrene-divinylbenzene copolymer.

Group (iii): Ion exchangers obtained by polymerization or copolymerization of monomers having an ethylenically unsaturated group, the monomers containing 8 to 80% by weight of a cross-linkable monomer based on the total weight of the monomers. Preferred cation exchangers of this group are sulfonated products of a cross-linked high molecular weight polymer prepared by addition copolymerization of styrene and vinyltoluene with 8 to 80% by weight of divinylbenzene based on the total weight of monomers as the main monomer components; sulfonated products of a cross-linked polymer prepared by addition copolymerization of, as the main monomer components, a monomer having an active group such as chloromethylstyrene, methylethyl ketone, epoxybutadiene and acrylamide with 8 to 80% by weight, based on the total weight of monomers, of a cross-linkable monomer such as divinylbenzene and triallyl cyanurate; and polymers prepared by copolymerization of, as the main monomer component, a monomer having a functional group capable of becoming an ion exchangeable group such as methacrylic acid, acrylic acid, their esters such as alkyl esters and phenyl esters, and 8 to 80% by weight of a cross-linkable monomer based on the total weight of monomers.

The monomers which can be employed in preparing the skeleton of cation exchangers in this invention include styrene and styrene derivatives such as methylstyrene, ethylstyrene, vinylnaphthalene, 3,4,6-trimethylstyrene, chlorostyrene, methoxystyrene, N,N-dimethylaminostyrene, nitrostyrene, chlorostyrene, trifluorostyrene, trifluoromethylstyrene and aminostyrene; butadiene; acrylonitrile and acrylonitrile derivatives; acrylic acid and acrylates such as methyl acrylate and chloromethyl acrylate; methacrylic acid and methacrylates such as cyclohexyl methacrylate, dimethylaminoethyl methacrylate, glycidyl methacrylate and methyl methacrylate; maleates such as diethyl maleate; fumarates such diethyl fumarate; vinyl ketones such as methyl vinyl ketone and ethyl isopropyl ketone; vinylidenes; acrylamide and acrylamide derivatives; aliphatic acid vinyl esters such as vinyl acetate, vinyl butylate and vinyl caproate; epoxybutadiene; sulfur-containing compounds such as styrenesulfonic acid, styrenesulfonates including styrenesulfonic acid butyl ester, and methylvinyl sulfide.

The cross-linkable monomers which can be employed in preparing the skeleton of cationic exchangers in this invention include divinylbenzene, divinyltoluene, divinylnaphthalene, divinylethylbenzene, trivinylbenzene, divinyldiphenylmethane, divinylbenzyl, divinylsulfone, divinylketone, bis(vinylpyridinoethyl)ethylene diamine, diallyl phthalate, triallyamine, N,N'-ethylenediacrylamide, ethylene glycol dimethacrylate, triethylene glycol dimethacrylate, trimethylolpropane trimethacrylate, trimethylolpropane triacrylate, triallyl isocyanurate and diallyl melamine.

Preferred cation exchangers are sulfonated products of a cross-linked high molecular weight polymer prepared by addition copolymerization of styrene, vinyltoluene and ethylbenzene with divinylbenzene as the main monomer components; sulfonated products of a cross-linked polymer prepared by addition copolymerization of, as the main monomer components, a monomer having an active group such as chloromethylstyrene, methylethyl ketone, epoxybutadiene and acrylamide with a cross-linkable monomer such as divinylbenzene or triallyl cyanurate; polymers prepared by polymerization of, as the main monomer component, a monomer having a sulfur atom capable of becoming an ion exchangeable group such as a styrenesulfonate including styrenesulfonic acid butyl ester or methylvinyl sulfide, or if desired, prepared by copolymerization of such a monomer is having a sulfur atom capable of becoming an ion exchangeable group with a cross-linking monomer or reaction products with such a monomer as having a sulfur atom capable of becoming an ion exchangeable group; and a polycondensate of phenol sulfonic acid with formaldehyde.

The cation exchanger having the above described characteristic conditions can be easily prepared from styrene-divinylbenzene copolymers as the starting materials.

A preferred method of producing particles of the cation exchanger is a suspension polymerization method. In conducting the addition polymerization or the polycondensation of oil-soluble monomers, it is preferred to employ an oil-in-water suspension and by selecting appropriate conditions without sieving, a narrow particle distribution can be obtained. Also in conducting the addition polymerization or the polycondensation of water-soluble monomers, it is necessary to employ a water-in-oil suspension. It is more difficult to obtain the water-in-oil suspension technically than to obtain the oil-in-water suspension. However, if only it is possible to prepare suspension-water pearls, a comparatively narrow particle distribution of polymers can be produced.

In the case of using oil-soluble monomers, the suspension may contain a viscous substance such as gum arabi, gamboge, rosin, pectin, an alginate, tragacanth gum, agar, methyl cellulose, starch, carboxymethyl cellulose, and gelatin; a synthetic high molecular weight substance such as sodium polyacrylate, polyvinyl alcohol, polyvinyl pyrrolidone and diacetoolein; and an inorganic substance such as hydrated magnesium silicate, titanium oxide, zinc oxide, calcium carbonate, talc, barium sulfate, calcium phosphate, aluminum hydroxide and silicic acid anhydride and, if necessary or if desired, a salt such as sodium chloride, a pH controlling agent and an emulsifier.

Also it is preferred to additionally employ a surfactant in suspending water in oil. Exemplary surfactants include sorbitan fatty acid esters, sorbitan fatty acid ester ethers, fatty acid soap and fatty acid glycerides.

The retaining agents which can be preferably employed in this invention include ions of Pb(II), Pd(II), Ni(II), V(IV)O, Cu(II), Hf(IV), Zr(IV), Ga(III), Ti(III), In(III), Fe(III) and V(III) and hydrogen ion. Of these ions, hydrogen ion is preferred.

The complexing agents which can be employed in this invention include aminopolyacetic acids such ethylene diamine tetracetic acid (hereinafter referred to as EDTA), 1,2-diaminocyclohexane tetracetic acid (hereinafter referred to as DCTA), N-hydroxyethyl ethylene diamine tetracetic acid, ethylene glycol-bis(2-aminoethyl)ether-N,N,N',N'-tetracetic acid, diethylene tetramine pentacetic acid, bis(2-aminoethyl)-ether-N,N,N',N'-tetracetic acid, nitrotriacetic acid and iminodiacetic acid and oxycarboxylic acids such as citric acid, lactic acid, glycolic acid, malic acid and tartaric acid.

The rare earth metals, the retaining agents and the complexing agents according to this invention are typically employed in the form of aqueous solutions.

The rare earth metal concentration ranges from about 1 mM/l to about 100 mM/l, the retaining agent concentration ranges from about 10 mM/l to about 5,000 mM/l and the complexing agent concentration ranges from about 1 mM/l to about 200 mM/l.

Various additives such as other solvents and stabilizers may be further added to the aqueous solutions. Exemplary additives include acetone, methyl ethyl ketone, dioxane, imidazole, 2-mercaptoethanol, ethylene diamine, thioglycolic acid, methanesulfonic acid, acetonylacetone, sulfamic acid, nitromethane, dimethylacetal, diethylene glycol, propylene glycol, tetrahydrofuran, pyridine, monoethanolamine, 2-aminopyridine, 3-amino-1,2 4-triazole, piperazine, methyl cellosolve, t-butanol, dimethylformamide, N-methylformamide, acetonitrile, acetylacetone, urea and oxine.

The pH of a retaining agent solution is adjusted in such a manner that the retaining agent does not form a precipitate by hydrolysis and the retaining agent has adsorbability to the cation exchanger. The pH of the retaining agent solution varies depending upon the retaining agent employed. For example, with Cu(II) as the retaining agent, the pH is typically about 0.1 to about 6.9 and preferably 1 to 4 and with hydrogen ion as the retaining agent, the concentration of hydrogen ion is typically at least about 0.01 M/l and preferably about 0.1 M/l to about 5 M/l.

The pH of a rare earth metal solution is adjusted in such a manner that the rare earth metals in the feed mixture do not form precipitates by hydrolysis and that the rare earth metals form complexes with a complexing agent if present. A complex formation can easily be calculated on the basis of their dissociation constants. A preferred pH of the rare earth metal solution is determined by the dissociation constant of the complexing agent. The pH is typically about 0.1 to about 10 and preferably about 1 to about 6. For example, with EDTA as the complexing agent, a preferred pH is about 2 to about 4.

It is necessary to adjust the pH of a complexing agent solution for developing a rare earth metal adsorption zone in such a manner that at the contact of the complexing agent with rare earth metal ions, formation of complexes between the rare earth metal ions and the complexing agent proceeds without causing precipitates due to the hydrolysis of the rare earth metal ions and thus reducing the absorbability of the rare earth metal ions to the cation exchanger. Generally, the pH of the complexing agent solution is adjusted in a state where the dissociation of the complexing agent is proceeding. For example, with EDTA as the complexing agent, the pH is typically about 4 to about 11 and preferably about 5 to about 8.

Acids or alkalis are employed in the regeneration of cation exchangers and the control of the pH of solutions. The acids and in alkalis which can be employed in this invention include inorganic acids such as hydrochloric acid, sulfuric acid, nitric acid, perchloric acid, hydrobromic acid and any mixture thereof; and sodium hydroxide, potassium hydroxide, lithium hydroxide, calcium hydroxide, magnesium hydroxide, barium hydroxide, sodium carbonate, potassium carbonate, lithium carbonate and aqueous ammonia. Of these acids and alkalis, sulfuric acid and hydrochloric acid as an acid and aqueous ammonia as an alkali are preferred from an economical viewpoint and due to their easy handling.

Any conventional methods for the separation of rare earth metals by using a cation exchanger may be employed in this invention. A typical chromatographical displacement process comprises the steps of:

(a) Passing a retaining agent solution to a developing column packed with the above described cation exchanger to adsorb the retaining agent on the cation exchanger, (b) Feeding a solution containing a mixture of rare earth metals alone or together with a complexing agent to the developing column to form a rare earth metal adsorption zone, (c) Feeding a complexing agent solution to the developing column to develop the rare earth metal adsorption zone by displacement, and (d) Collecting the eluant flowing from the developing column in fractions at the outlet of the developing column with the passage of the development.

If the separation of the rare earth metal is not sufficient, the outlet of the above described developing column is connected with the inlet of another developing column packed with the cation exchanger on which the retaining ion has been adsorbed, and the separation of the rare earth metal is continued by continuously transferring the rare earth metal adsorption zone from one developing column to another until a sufficient separation of the rare earth metal is obtained and an eluant from a last developing column is collected in fractions.

The cation exchanger of this invention has a high exchange rate and accordingly, the boundaries between any two rare earth metals become sharp. As a result, a total length of the rare earth metal adsorption zone which is required for efficiently obtaining products can be shortened and products having a high purity can be obtained in a short period of time by using a separation apparatus of a small size.

In making the most of the above-described characteristic feature, the migration velocity which can be preferably employed in this invention is at least about 5 m per day and its upper limit is determined by the pressure drop in the developing column employed. For practical purposes, a preferred migration velocity of the rare earth metal adsorption zone ranges from about 5 m per day to about 500 m per day.

Further, it is preferred to employ at least two developing columns in the process of this invention in order to efficiently effect the separation of rare earth metals at a high speed.

Moreover, the highly efficient, high speed separation of rare earth metals can be conducted in a closed system by using hydrogen ion as the retaining agent, passing a solution containing at least about 0.01 M/l of hydrogen ion through a developing column where a rare earth metal adsorption zone has already passed to convert the cation exchanger in its hydrogen ion type and withdrawing the formed neutral salt flowing from the developing column out of the separation system to reuse the complexing agent at a high speed.

The separation of rare earth metals according to this invention can be preferably conducted at a temperature ranging from about 0° C. to about 150° C. which varies depending upon the retaining agent employed, the complexing agent chosen and other factors. A preferred temperature ranges from about 10° C. to about 120° C. For example, when hydrogen ion is used as the retaining agent and EDTA or DCTA is used as the complexing agent, a preferred temperature ranges from about 70° C. to about 150° C. and a more preferred temperature ranges from about 85° C. to about 120° C. When Fe(III) ion is used as the retaining agent and EDTA is used as the complexing agent, a preferred temperature ranges from about 10° C. to about 60° C.

In conducting the migration of a rare earth adsorption zone at such a temperature comparatively higher than about 10° C. as described above, when the temperature of solutions fed to a developing column packed with the cation exchanger, especially the temperature of the complexing agent solution is different from the predetermined and maintained inner temperature of the developing column, it becomes difficult to reduce the overlapping of the adsorption zone of one rare earth metal which has been formed with the progress of separation on the cation exchanger and the adsorption zone of an adjacent rare earth metal, i.e. to form a sharp boundary between the two rare earth metal absoprtion zones. As a result, the separation efficiency is reduced and control of the separation system tends to be difficult. Thus, it is preferred to keep the temperature difference of the solutions fed to the developing column and the predetermined and maintained inner temperature of the developing column at no more than ±10° C. A more preferred temperature difference is within ±5° C. and especially ±2° C.

The process of this invention will now be illustrated in greater detail by reference to the following examples but these examples are not to be interpreted as limiting the invention in any way.

EXAMPLE 1

In three columns X, Y and Z, each having an inside diameter of 2 cm and a length of 100 cm was packed a sulfonated product of a cross-linked styrene-divinylbenzene copolymer having an average particle diameter of 86μ in its hydrogen form as the cation exchanger up to a height of 90 cm. The kinds of the cation exchangers in the columns X, Y and Z were as follows;

| Column | Degree of Cross-linking | Micro-void Volume Ratio |
| --- | --- | --- |
| X | 20 | 0.45 |
| Y | 20 | 0.55 |
| Z | 20 | 0.85 |

Then the temperature of the colums X, Y and Z was maintained at 30° C. and to the top of the columns X, Y and Z was supplied an aqueous solution containing 20 mM/l of copper (II) chloride 2 hydrates and 0.012 M/l of hydrogen ion at a rate of 125 ml per minute to convert the cation exchanger in its Cu(II) ion form. Then an aqueous solution containing 8 mM/l of neodymium (III) chloride, 8 mM/l of praseodymium (III) chloride, 20 mM/l of EDTA and 0.012 M/l of hydrogen ion was supplied to the top of each of the columns X, Y and Z at a rate of 39.5 ml per minute for 143 minutes. Subsequently an aqueous solution containing 20 mM/l of EDTA and 18 mM/l of sodium hydroxide was supplied to the top of each of the columns X, Y and Z and from the bottom of each of the columns X, Y and Z was collected a developed solution in separate fractions by a fraction collector. The migration velocity of the rare earth metal adsorption zone in each of the columns X, Y and Z was 10 m per day. The amount of praseodymium was quantitatively analyzed by X-ray fluorometry. As a result, the recovery rate of praseodymium having a purity of at least 99.9% was as follows;

| Column | Recovery Rate (weight %) |
| --- | --- |
| X | 12 |
| Y | 57 |
| Z | 64 |

EXAMPLE 2

In a jacketed separating column having an inside diameter of 2 cm and a length of 100 cm was packed a cation exchanger as set forth in Table 1 uniformly up to a height of 90 cm, and 2.0 l of 0.5 M/l sulfuric acid solution were fed to the top of the column to convert the packed cation exchanger in its hydrogen ion form. Then the temperature of the column was maintained at 95° C. and to the top of the column was fed an aqueous solution containing 7.5 mM/l of neodymium, 7.5 mM/l of praseodymium and 15 mM/l of EDTA and having a pH of 3.0 until the length of a rare earth metal adsorption zone reached 60 cm. Subsequently an aqueous solution containing 15 mM/l of EDTA and having a pH of 7.0 was fed to the top of the column at such a flow rate that the migration velocity of the rare earth metal adsorption zone became the one as set forth in Table 1 to develop the uranium adsorption zone by displacement. The eluant flowed from the bottom of the column in accordance with the development was collected as separate fractions of 15 ml and the amount of neodymium and praseodymium was quantitatively analyzed by X-ray fluorometry. As a result, praseodymium having a purity of at least 99.9% was obtained in an amount as set forth in Table 1 together with the separated amount of praseodymium having a purity of at least 99.9% per hour.

90° C. and to the top of the column was fed an aqueous solution containing 7.5 mM/l of neodymium, 7.5 mM/l of praseodymium and 15 mM/l of EDTA and having a pH of 3.0 until the length of a rare earth metal adsorption zone reached 120 cm. Subsequently an aqueous solution containing 15 mM/l of EDTA and having a pH of 7.0 was fed to the top of the column at such a flow

TABLE 1

| | | Cation Exchanger | | | Developing Conditions | | Result | |
|---|---|---|---|---|---|---|---|---|
| | Kind | Micro-void Volume Ratio | Degree of Cross-linking | Average Particle Diameter (μ) | Migration Velocity (meter/day) | Time*1 (hour) | Pr*2 (mmol) | Pr*2/ hour (mmol/hour) |
| Run No. | | | | | | | | |
| 1 | Sulfonated vinyltoluene-divinylbenzene copolymer | 0.58 | 10 | 190 | 4.5 | 8 | 4.88 | (0.61) |
| 2 | Sulfonated vinyltoluene-divinylbenzene copolymer | 0.58 | 10 | 190 | 20 | 1.8 | 2.74 | (1.52) |
| 3 | Sulfonated styrene-divinylbenzene copolymer | 0.65 | 20 | 195 | 20 | 1.8 | 3.82 | (2.12) |
| 4 | Sulfonated styrene-divinylbenzene copolymer | 0.71 | 30 | 105 | 47 | 0.766 | 6.21 | (8.11) |
| 5 | Vinylsulfonic acid-divinylbenzene copolymer | 0.85 | 70 | 151 | 230 | 0.156 | 1.44 | (9.2) |
| 6 | Product prepared by copolymerizing chloromethylstyrene and divinylbenzene, reacting the obtained copolymer with thiourea, hydrolyzing the reaction product with sodium hydroxide and oxidizing the product with hydrogen peroxide | 0.76 | 23 | 45 | 8 | 4.5 | 15.8 | (3.51) |
| 7 | Sulfonated styrene-divinylbenzene copolymer | 0.68 | 25 | 87 | 24 | 1.5 | 12.1 | (8.07) |
| Comparative Run No. | | | | | | | | |
| 1 | Sulfonated vinyltoluene-divinylbenzene copolymer | 0.47 | 10 | 191 | 4.5 | 8 | 1.76 | (0.22) |

Note:
*1Time required for separation of rare earth metals
*2Praseodymium having a purity of at least 99.9%

EXAMPLE 3

In a jacketed separating column having an inside diameter of 5 cm and a length of 200 cm was packed a sulfonated product of a styrene-divinylbenzene copolymer having a micro-void volume ratio, a degree of cross-linking and an average particle diameter as set forth in Table 2 as the cation exchanger uniformly up to a height of 190 cm, and 2.0 l of 0.5 M/l sulfuric acid solution were fed to the top of the column to convert the packed cation exchanger in its hydrogen ion form. Then the temperature of the column was maintained at rate that the pressure drop between the top and the bottom of the column became 10 Kg/cm² to develop the uranium adsorption zone by displacement. The eluant flowed from the bottom of the column in accordance with the development was collected as separate fractions of 100 ml and the amount of neodymium and praseodymium was quantitatively analyzed by X-ray fluorometry. As a result, praseodymium having a purity of at least 99.9% was obtained in an amount as set forth in Table 2 together with the separated amount of praseodymium having a purity of at least 99.9% per hour.

TABLE 2

| | Cation Exchanger | | | Developing Conditions | | Result | |
|---|---|---|---|---|---|---|---|
| | Micro-void Volume Ratio | Degree of Cross-linking | Average Particle Diameter (μ) | Migration Velocity (meter/day) | Time*1 (hour) | Pr*2 (mmol) | Pr*2/ hour (mmol/hour) |
| Run No. | | | | | | | |
| 1 | 0.70 | 8 | 78 | 18 | 6.8 | 192 | (28.7) |
| 2 | 0.69 | 23 | 80 | 20 | 4.08 | 211 | (52) |
| 3 | 0.72 | 60 | 77 | 26 | 3.1 | 164 | (53) |
| 4 | 0.69 | 23 | 45 | 6.1 | 13.4 | 235 | (17.5) |
| 5 | " | " | 175 | 94 | 0.87 | 38.2 | (44) |
| 6 | " | " | 25 | 1.9 | 43 | 241 | (5.6) |
| 7 | " | " | 200 | 119 | 0.69 | 12.7 | (14.3) |
| Comparative Run No. | | | | | | | |

TABLE 2-continued

| | Cation Exchanger | | | Developing Conditions | | | Result | |
|---|---|---|---|---|---|---|---|---|
| | Micro-void Volume Ratio | Degree of Cross-linking | Average Particle Diameter ($\mu$) | Migration Velocity (meter/day) | Time*1 (hour) | Pr*2 (mmol) | $\left\{\begin{array}{l}\text{Pr*2/}\\\text{hour}\\\text{(mmol/hour)}\end{array}\right.$ | |
| 1 | 0.45 | 15 | 25 | 1.1 | 74 | 156 | (2.1) | |
| 2 | 0.43 | 10 | 200 | 92 | 0.89 | Not obtained | | |

Note:
*1 Time required for separation of rare earth metals
*2 Praseodymium having a purity of at least 99.9%

EXAMPLE 4

FIG. 1 shows the apparatus employed in this Example. The apparatus included three developing columns I, II and III, each having an inside diameter of 2 cm and a length of 2 m and equipped with a jacket. Each column was uniformly packed with a sulfonated product of a styrene-divinylbenzenecopolymer having a microvoid volume ratio of 0.69, a degree of cross-linking of 23 and an average particle diameter of 112$\mu$ as the cation exchanger up to a height of 1.9 m. Multi-way valves, a, b, c, d, e and f, each was connected to the inlet and the outlet of developing columns I, II and III, respectively. Furthermore, the apparatus included three liquid-supply pumps A, B and C; three storage tanks 1, 2 and 3 for a rare earth metal solution, a retaining agent solution and a complexing agent solution, respectively; a fraction collector 4 for a product; and a tank 5 for waste.

An aqueous rare earth metal solution, an aqueous retaining agent solution and an aqueous complexing agent solution were charged in storage tanks 1, 2 and 3 in amounts as set forth in Table 3, respectively and the separation of rare earth metals was conducted as follows;

(1) The cation exchanger in developing columns I, II and III was successively converted to its hydrogen ion form by supplying the retaining agent solution by operating liquid-supply pump B through route 2-B-a-I-d, 2-B-b-II-e and 2-B-c-III-f.

(2) The operation of liquid-supply pump B was stopped and that of liquid-supply pump C was started and the rare earth metal solution was fed to developing columns III and I successively through route 1-A-c-III-f-a-I-d to form a rare earth metal adsorption zone and to conduct development and migration of the rare earth metal adsorption zone from developing column III to developing column I.

(3) When the length of the rare earth metal adsorption zone reached 3.6 m, the operation of liquid-supply pump A was stopped and that of liquid-supply pump C was started and the complexing agent solution was supplied to developing columns III and I successively through route 3-C-c-III-f-a-I. Multi-way valve d was connected with multi-way valve b at the same time as the start of operation of liquid-supply pump C and the eluant from developing column I was withdrawn through route I-d-b-II-e-5.

(4) When the frontal portion of the rare earth metal adsorption zone reached the position 10 cm above the bottom of the packed cation exchanger layer in developing column II in accordance with the progress of development, multi-way valve f was disconnected from multi-way valve a and the retaining agent solution was supplied to developing column III by operating liquid-supply pump B through route 2-B-c-III-f-5. Simultaneously the complexing agent solution was fed to developing columns I and II successfully by liquid-supply pump C through route 3-C-a-I-d-b-II, and the eluant from developing column II was collected in separate fractions of 50 ml by fraction collector 4 through route II-e-4.

(5) When the retaining agent solution began to flow from the bottom of developing column III, the operation of liquid-supply pump B was stopped and that of liquid-supply pump A was started and the rare earth metal solution was supplied to developing column III through route 1-A-c-III.

(6) When the migration of the rare earth metal absorption zone from developing column I to developing column II was completed in accordance with the above-described step 4 and the rear portion of the rare earth metal absorption zone reached the position 10 cm below the top of the packed cation exchanger layer in developing column II, multi-way valve d was disconnected from multi-way valve b and the complexing agent solution was supplied to developing column II by liquid-supply pump C through route 3-C-b-II-e-4 to develop the rare earth metal adsorption zone in developing column II and to conduct its migration. On the other hand, by the operation of liquid-supply pump B the retaining agent solution and fed to developing column I through route 2-B-a-I-d until the retaining agent solution began to flow from the bottom of developing column I.

(7) When the retaining agent solution began to flow from the bottom of developing column I, the operation of liquid-supply pump B was stopped and multi-way valve f was connected with multi-way valve a and the eluant from developing column III was led to developing column I through route III-f-a-I.

(8) When the rare earth metal absorption zone began to flow from the bottom of developing column II, the operation of liquid-supply pump C was stopped and that of liquid-supply pump B was started and the retaining agent solution was supplied to developing column II through route 2-B-b-II until the retaining agent solution began to flow from the bottom of developing column II. Then the operation of liquid-supply pump B was stopped.

(9) Subsequently the above-described steps (3) to (8) were repeated. The feed rare earth metal solution was supplied five times to conduct the separation of rare earth metals.

The retaining agent solution, the complexing agent solution, the rare earth metal solution and the development conditions employed in the above-described procedures and the results are shown in Table 3.

TABLE 3

| | Feed Solutions | | | Developing Conditions | | | | Result | |
|---|---|---|---|---|---|---|---|---|---|
| Run No. | Retaining Agent Solution | Complexing Agent Solution | Rare Earth Metal Solution (mM/l) | Temperature*1 (°C.) | Pressure Drop in Each Column (Kg/cm$^2$) | Migration Velocity (meter/day) | Time*2 (hour) | Pr*3 (mM) | Pr*3/hour (mM/hour) |
| 1 | The same as in Example 1 200 l | The same as in Example 1 200 l | Pr(III)Cl$_3$ 8<br>Nd(III)Cl$_3$ 8<br>EDTA 20<br>150 l | 95 | 10 | 35 | 22.4 | 585 | (26.1) |
| 2 | The same as in Example 2 40 l | The same as in Example 2 200 l | Pr(III)Cl$_3$ 7.5<br>Nd(III)Cl$_3$ 7.5<br>EDTA 15<br>100 l | 95 | 10 | 42 | 19.04 | 418 | (22.0) |

Note:
*1 Temperature employed for separation of rare earth metals
*2 Time required for separation of rare earth metals
*3 Praseodymium having a purity of at least 99.9% by analysis by X-ray fluorometry

EXAMPLE 5

Figure 2:
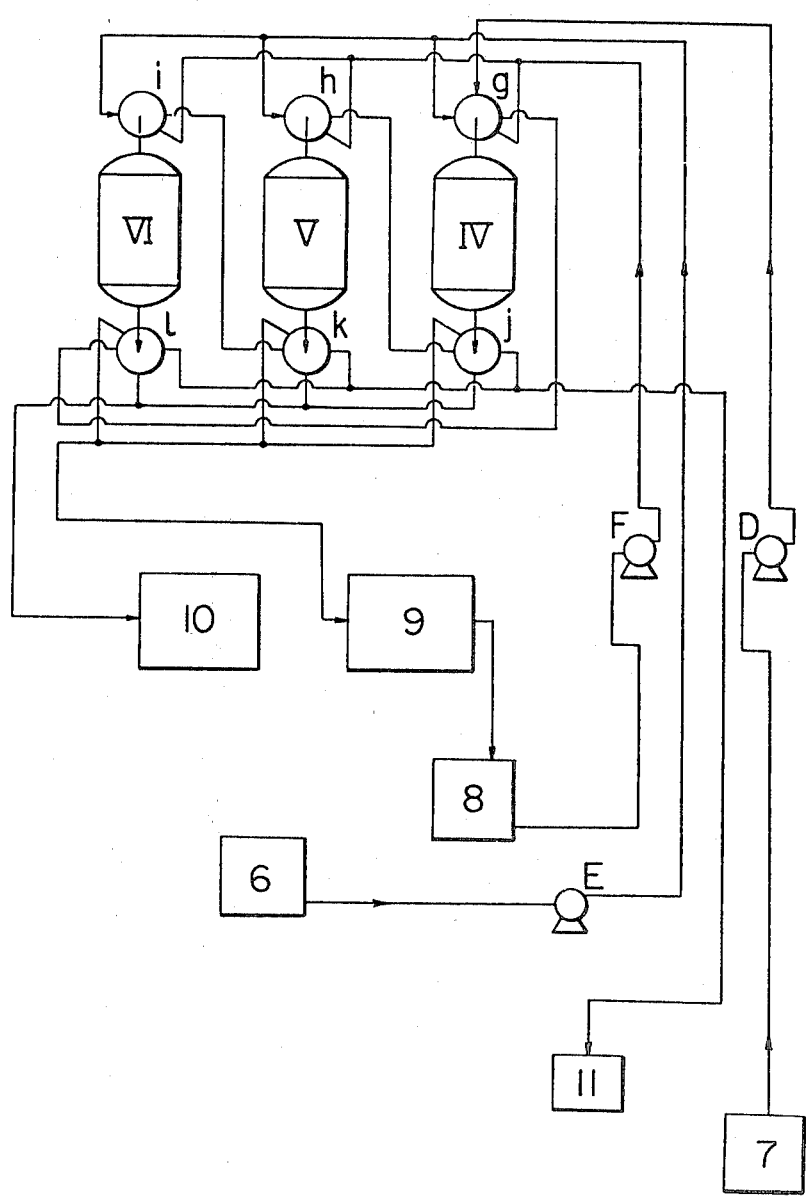
FIG. 2 illustrates the flow diagram of an apparatus of another embodiment wherein three developing columns are employed.

FIG. 2 shows the apparatus employed in this Example. The apparatus included three developing columns IV, V and VI, each having an inside diameter of 2 cm and a length of 2 m and equipped with a jacket. Each column was packed with, as the cation exchanger, a sulfonated product of a cross-linked styrene-divinylbenzene copolymer having a micro-void volume ratio of 0.72 an average particle diameter of 87μ and a degree of cross-linking of 35 up to a height of 1.9 m. Each of multi-way valves g, h, i, j, k and l, each was connected to the inlet and the outlet of developing columns IV, V and VI, respectively. Furthermore, the apparatus included three liquid-supply pumps D, E and F; three storage tanks 6, 7 and 8 for a retaining agent solution, a rare earth metal solution and a complexing agent solution, respectively; a tank 9 for collecting a solution containing the complexing agent; a tank 10 for waste; and a fraction collector 11 for a product.

In storage tank 6 were charged 40 l of an aqueous solution containing 0.5 M/l of sulfuric acid, as the retaining agent solution, where hydrogen ion acted as a retaining agent and in storage tank 7 were charged 100 l of an aqueous solution containing 7.5 mM/l of praseodymium (III) sulfate, 7.5 mM/l of neodymium (III) sulfate and 15 mM/l of EDTA. In storage tank 8 were charged 150 l of an aqueous solution containing 15 mM/l of EDTA and having a pH of 7.

(1) The cation exchanger in developing columns IV, V and VI was successively converted to that of the hydrogen ion form by supplying the retaining agent solution by operating liquid-supply pump E through route 6-E-g-IV-j, 6-E-h-V-k and 6-E-i-VI-l.

(2) The operation of liquid-supply pump E was stopped and that of liquid-supply pump D was started and the rare earth metal solution was fed to developing columns IV and V successively through route 7-D-g-IV-j-h-V-k to form a rare earth metal adsoprtion and to conduct development and migration of the rare earth metal adsorption zone from developing column IV to developing column V. The eluant flowing from the bottom of developing column V corresponding to the void volume of the packed cation exchange layers in developing columns IV and V in accordance with the progress of development was transferred to tank 10 through route V-k-10 and the subsequent eluant was collected in tank 9 through route V-k-9 and then transferred to storage tank 8 for the complexing agent solution where its pH was adjusted to 7 with an aqueous ammonia solution.

(3) When the length of the rare earth metal adsorption zone reached 3.6 m, the operation of liquid-supply pump D was stopped and that of liquid-supply pump F was started and the complexing agent solution was supplied to developing column IV through route 8-F-g-IV. Multi-way valve k was connected with multi-way valve i at the same time as the operation of liquid-supply pump F was begun and the eluant from developing column V was fed to developing column VI through route V-k-i-VI and the eluant flowing from the bottom of developing column VI corresponding to the void volume of the packed cation exchanger layer in developing column VI was transferred to tank 10 through route VI-l-10 and the subsequent eluant from the bottom of development column VI was transferred to tank 9 through VI-l-9.

(4) When the frontal portion of the rare earth metal adsorption zone reached the position 10 cm above the bottom of the packed cation exchanger layer in developing column VI in accordance with the progress of development, multi-way valve j was disconnected from multi-way valve h and the retaining agent solution was supplied to developing column IV by operating liquid-supply pump E through route 6-E-g-IV-j-10. Simultaneously the complexing agent solution was fed to developing columns V and VI successively by operating liquid-supply pump F through route 8-F-h-V-k-i-VI, and the eluant from developing column VI was collected in separate fractions of 50 ml by fraction collector 11 through route VI-l-11.

(5) When the retaining agent solution began to flow from the bottom of developing column IV, the operation of liquid-supply pump E was stopped and that of liquid-supply pump A pump D was started and the rare earth metal solution was supplied to developing column IV.

(6) When the migration of the rare earth metal adsorption zone from developing column V to developing column VI was completed in accordance with the above-described step 4 and the rear portion of the rare earth metal adsorption zone reached the position 10 cm below the top of the packed cation exchanger layer in deveopling column VI, multi-way valve k was disconnected from multi-way valve i and the complexing agent solution was supplied to developing column VI by liquid-supply pump F through route 8-F-i-VI-l to develop the rare earth metal adsorption zone in developing column VI and to conduct its migration. On the other hand, by the operation of liquid-supply pump E the retaining agent solution was fed to developiing column V through route 6-E-h-V-k until the retaining agent solution began to flow from the bottom of developing column V.

(7) When the retaining agent solution began to flow from the bottom of developing column V, the operation of lqiuid-supply pump E, was connected and multi-way valve j was connected with multi-way valve h and the eluant from developing column IV was led to developing column V through route IV-j-h-V.

(8) When the rare earth metal adsorption zone began to flow from the bottom of developing column VI, the operation of liquid-supply pump F was stopped and that of liquid-supply pump E was started and the retaining agent solution was supplied to developing column VI through route 6-F-i-VI until the retaining agent solution began to flow from the bottom of developing column VI. Then the operation of liquid-supply pump E was stopped.

(9) Subsequently the above-described steps (3) to (8) were repeated by supplying the feed rare earth metal five times to conduct the separation of rare earth metals.

The migration velocity of the rare earth metal adsorption zone was 53 m/day, the temperature employed for the separation was 95° C. and the time required for the separation was 15.3 hours. As the result of analysis by X-ray fluorometry were obtained 461 mM of praseodymium having a purity of 99.9%.

What is claimed is:

1. In a process for the separation of one rare earth metal from another in a mixture of rare earth metals by passing a retaining agent solution through a bed of a cation exchanger to convert the cation exchanger into that of a retaining agent type, passing a solution of the mixture through the cation exchanger to form a rare earth metal adsorption zone on the bed of the cation exchanger, passing a complexing agent solution through the cation exchanger to effect migration of the rare earth metal adsorption zone through the bed of the cation exchanger and separating a fraction of one of the rare earth metals, the improvement which comprises using as the cation exchanger a cation exchanger having a micro-void volume ratio of 0.58 to 0.95 and a degree of crosslinking of 8 to 17 or having a micro-void volume ratio of 0.50 to 0.95 and a degree of crosslinking of 17 to 80 and passing the materials through the cation exchanger at a rate such that the migration velocity of the rare earth metal adsorption zone through the cation exchanger is from about 5 m per day to about 500 m per day.

2. The process of claim 1, wherein the cation exchanger has a micro-void volume ratio of 0.50 to 0.95 and a degree of crosslinking of 17 to 80.

3. The process of claim 2, wherein the cation exchanger has a micro-void volume ratio of 0.50 to 0.88.

4. The process of claim 2, wherein the cation exchanger has a micro-void volume ratio of 0.55 to 0.82.

5. The process of any one of claims 1, 2, 3, or 4 which comprising using hydrogen ion as the retaining agent, passing a solution containing at least about 0.01 M/l of hydrogen ion through the bed of the cation exchanger where the rare earth metal adsorption zone has already passed to convert the cation exchanger into that of a hydrogen ion type, and withdrawing the formed neutral salt from the bed of the cation exchanger.

6. The process of any one of claims 2, 3 or 4, wherein the cation exchanger is obtained by polymerization or co-polymerization of monomers having an ethylenically unsaturated group and containing at least 17% by weight of a crosslinkable monomer based on the total weight of the monomers.

7. The process of claim 6, comprising using hydrogen ion as the retaining agent, passing a solution containing at least about 0.01 M/l of hydrogen ion through the bed of the cation exchanger where the rare earth metal adsorption zone has already passed to convert the cation exchanger into that of a hydrogen ion type, and withdrawing the formed neutral salt from the bed of the cation exchanger.

8. In a process for the separation of one rare earth metal from another in a mixture of rare earth metals by passing a retaining agent solution through a bed of a cation exchanger to convert the cation exchanger into that of a retaining agent type, passing a solution of the mixture through the cation exchanger to form a rare earth metal adsorption zone on the bed of the cation exchanger, passing a complexing agent solution through the cation exchanger to effect migration of the rare earth metal adsorption zone through the bed of the cation exchanger and separating a fraction of one of the rare earth metals, the improvement which comprises using as the cation exchanger a cation exchanger having a micro-void volume ratio of 0.50 to 0.95 and a degree of crosslinking of 17 to 80 and passing the materials through the cation exchanger at a rate such that the migration velocity of the rare earth metal adsorption zone through the cation exchanger is from about 5 m per day to about 500 m per day.

9. The process of claim 8, wherein the cation exchanger has a micro-void volume ratio of 0.50 to 0.88.

10. The process of claim 9, wherein the cation exchanger has a micro-void volume ratio of 0.55 to 0.82.

* * * * *